United States Patent [19]

Schreinemakers

[11] Patent Number: 5,190,457

[45] Date of Patent: Mar. 2, 1993

[54] METHOD FOR MAKING AN IMPRESSION OF A DENTATE HUMAN JAW

[76] Inventor: Josephus Schreinemakers, Oranje Nassaulaan 12, NL-60 26 BX Maarheeze, Netherlands

[21] Appl. No.: 884,750

[22] Filed: May 15, 1992

[30] Foreign Application Priority Data

May 17, 1991 [DE] Fed. Rep. of Germany ....... 4116109
Jan. 31, 1992 [DE] Fed. Rep. of Germany ....... 4202676

[51] Int. Cl.⁵ ............................................. A61C 9/00
[52] U.S. Cl. ..................................... 433/214; 433/37
[58] Field of Search ............................. 433/37, 214

[56] References Cited

U.S. PATENT DOCUMENTS

| | | | |
|---|---|---|---|
| 1,778,293 | 10/1930 | Galasso | 433/37 |
| 2,311,158 | 2/1943 | Conway et al. | 433/214 |
| 3,882,601 | 5/1975 | Jahn | 433/214 |
| 4,085,507 | 4/1978 | Lehn et al. | 433/37 |
| 4,684,343 | 8/1987 | Schreinemakers | 433/214 |

FOREIGN PATENT DOCUMENTS

2630905 11/1989 France ................................ 433/214

*Primary Examiner*—John J. Wilson
*Attorney, Agent, or Firm*—Herbert Dubno; Andrew Wilford

[57] ABSTRACT

A bead of a high-viscosity impression material is applied along the entire edge of an imperforate tray forming a U-shaped recess and an endless edge extending all around the recess and the tray is fitted, before the material cures, over a patient's dental arch with the bead on the edge engaging and deformed by the patient's mobile mucosa outward of the linear action boundary. The deformed bead of high-viscosity material is cured to form the tray and the cured bead of high-viscosity material into a custom tray which is then filled with a body of a low-viscosity impression material and again pressed over the patient's dental arch to press the cured bead on the tray edge into tight engagement against the mobile mucosa outward of the linear action boundary to form between the tray and the dental arch a substantially closed and generally constant-section chamber hydraulically confining the low-viscosity impression material. The confined low-viscosity material in the chamber is then compressed against the dental arch by pressing the tray toward the arch while mobilizing the mobile mucosa to hydraulically press the confined material into form-fit engagement with the stationary mucosa and tooth and without substantial leakage of the impression material from the chamber and the low-viscosity impression material is cured. Finally the custom tray with the cured low-viscosity material is stripped from the patient's jaw.

14 Claims, 2 Drawing Sheets ately differently dimensioned such trays -->
METHOD FOR MAKING AN IMPRESSION OF A DENTATE HUMAN JAW

FIELD OF THE INVENTION

The present invention relates to a system for making an impression of a dentate human jaw. More particularly this invention concerns a method of making such an impression using a spoon or tray filled with a hardenable impression material.

BACKGROUND OF THE INVENTION

In my U.S. Pat. No. 4,684,343 I describe a method of using a U-shaped, U-section, and imperforate tray having a buccal edge and an opposite lingual/palatal edge to take an impression of a human patient's jaw having a hard U-shaped dental arch, a mobile mucosa and a stationary mucosa to each side thereof, at least one tooth, and a linear action boundary between the two mucosae. According to this earlier invention one first selects from a set of anatomically differently dimensioned such trays the tray capable of fitting over the dental arch of the current patient with the buccal edge outside the arch and the lingual/palatal edge within the arch, with the tray generally uniformly spaced at most 5 mm from the arch and with the buccal and lingual/palatal edges engaging the mobile mucosa generally beyond the linear action boundary. This tray is then filled with a high-viscosity impression material and the filled and selected tray is pressed over said current patient's dental arch to force the buccal and lingual/palatal edges into tight engagement against the mobile mucosa past the linear action boundary with the tray generally uniformly spaced at most 5 mm from the arch to form between the tray and the dental arch a substantially closed and generally constant-section chamber hydraulically confining the impression material. The confined material is then compressed in the chamber against the dental arch by pressing the tray toward the arch while mobilizing the mobile mucosa to hydraulically press the confined material into form-fit engagement with the stationary mucosa and without substantial leakage of the impression material from the chamber.

This system has proven itself to be very good, but still has two modest drawbacks:

First of all it is impractical to provide a set of impression trays that is large enough to ensure a good fit with any mandible or maxilla. The variation in human anatomy is so very great that a very tight fit is only rarely possible. Thus there is inevitably some leakage from the chamber and, as a result, the highly viscous impression material is not pressurized sufficiently to conform to all of the contours of the region being worked on. Using a less viscous material that would more easily get into the various recesses and undercuts is impossible in working on a dentate jaw since it is necessary as described in my earlier patent to make the impression of the hard dental structures, with the softer ones pushed back or out of the way, and such less viscous material would be even more likely to leak out of the chamber which, as described above, is rarely sealed perfectly. Furthermore the less viscous material is more likely to leak out of the tray, so it will be pressurized even less than the high-viscosity material.

In addition once the impression is made it is quite difficult to separate it from the jaw in question. Since the material gets into recesses and undercuts, and also since the high-viscosity impression material hardens to a fairly stiff body, pulling it off entails deforming it and subjecting the contacting jaw structures to substantial stress. Once again using a more easily deformed softer impression material would avoid this problem, but would not allow one to proceed hydraulically as described above.

Accordingly it is known to make a first impression using one of a standardized set of trays and a low-viscosity impression material. From this rough impression a rough positive model is made and a custom acrylic tray is then made that provides the desired 1 mm to 5 mm spacing. This custom tray is therefore a very good fit and it is subsequently used with a high-viscosity material in a pressurized hydraulic procedure to form a very accurate impression from which another model is made, and this second model is used to construct the inlay, crown, bridge, partial denture, or the like. Such a procedure produces excellent results but has the first disadvantage that it requires two different impressions and an extra positive model to be made, greatly increasing the difficulty and cost of the procedure, and, second, the high-viscosity material is still hard to strip off the jaw.

OBJECTS OF THE INVENTION

It is therefore an object of the present invention to provide an improved system for making an impression of a dentate human jaw.

Another object is the provision of such an improved system for making an impression of a dentate human jaw which overcomes the above-given disadvantages, that is which ensures that a very accurate impression of the hard dental structures can be taken, and that this impression can subsequently be stripped relatively easily from the jaw being worked on.

SUMMARY OF THE INVENTION

An impression of a human patient's jaw having a hard U-shaped dental arch, a mobile mucosa and a stationary mucosa to each side of the arch, a linear action boundary between the mucosae, and at least one tooth projecting from the arch is taken with an imperforate tray forming a U-shaped recess and an endless edge extending all around the recess. First a bead of a high-viscosity impression material is applied along the entire edge of the tray and same is fitted, before the material cures, over the arch with the bead on the edge engaging and deformed by the mobile mucosa outward of the linear action boundary. The deformed bead of high-viscosity material is cured to form the tray and the cured bead of high-viscosity material into a custom tray which is then filled with a body of a low-viscosity impression material and pressed over the patient's dental arch to press the cured bead on the tray edge into tight engagement against the mobile mucosa outward of the linear action boundary to form between the tray and the dental arch a substantially closed and generally constant-section chamber hydraulically confining the low-viscosity impression material. The confined low-viscosity material in the chamber is then compressed against the dental arch by pressing the tray toward the arch while mobilizing the mobile mucosa to hydraulically press the confined material into form-fit engagement with the stationary mucos and tooth and without substantial leakage of the impression material from the chamber and the low-viscosity impression material is cured. Finally the custom tray with the cured low-viscosity material is stripped from the patient's jaw.

Thus with the system of this invention a perfectly fitting custom tray is formed so that a fine-detail impression can be taken using a relatively low-viscosity material. The edges of the tray, which is selected from a set of such trays but is at best only an approximate fit, are custom formed to fit the patient's mouth and also are still somewhat resilient so that they can form a very tight seal with the mobile mucosa. The low-viscosity material is still hydraulically pressurized to get into every crack, recess, undercut, and crevice of the dental arch as the mobile mucosa and other mobile associated buccal structures are activated so that it will be able to work as well as the high-viscosity material of the prior art. Nonetheless since the tray fits perfectly there will be no significant chance of leakage and subsequent removal will be very easy.

According to the invention the low-viscosity impression material is cured to a Shore A hardness of at most 30, preferably at most 25 or even 20. The bead of high-viscosity material is applied along both the buccal and palatal/lingual portions of the tray. This bead can be formed by hand and applied to the tray edge.

In accordance with further features of the invention the high-viscosity impression material comprises polyvinylpolysiloxane have a viscosity when uncured of at least 200 Pa.sec and when cured of between 55 Shore A and 75 Shore A. The low-viscosity impression material comprises polyvinylpolysiloxane also but has a viscosity when uncured of at most 160 Pa.sec and when cured of at most 30 Shore A.

It is also possible according to a further feature of the invention to line at least a portion of the tray with a high-viscosity impression material over which the low-viscosity material is filled. The two materials cure at the same rate and in fact all of the impression materials merge integrally during the last curing step. The high-viscosity lining material is forced in fact into the sulcus of the tooth since it is applied in a layer 2 mm to 3 mm thick in the tray, that is about half filling it since the tray is spaced about at most 5 mm from the tooth outer surfaces.

BRIEF DESCRIPTION OF THE DRAWINGS

The above and other objects, features, and advantages will become more readily apparent from the following, reference being made to the accompanying drawing in which.

SPECIFIC DESCRIPTION

Figure 1A:
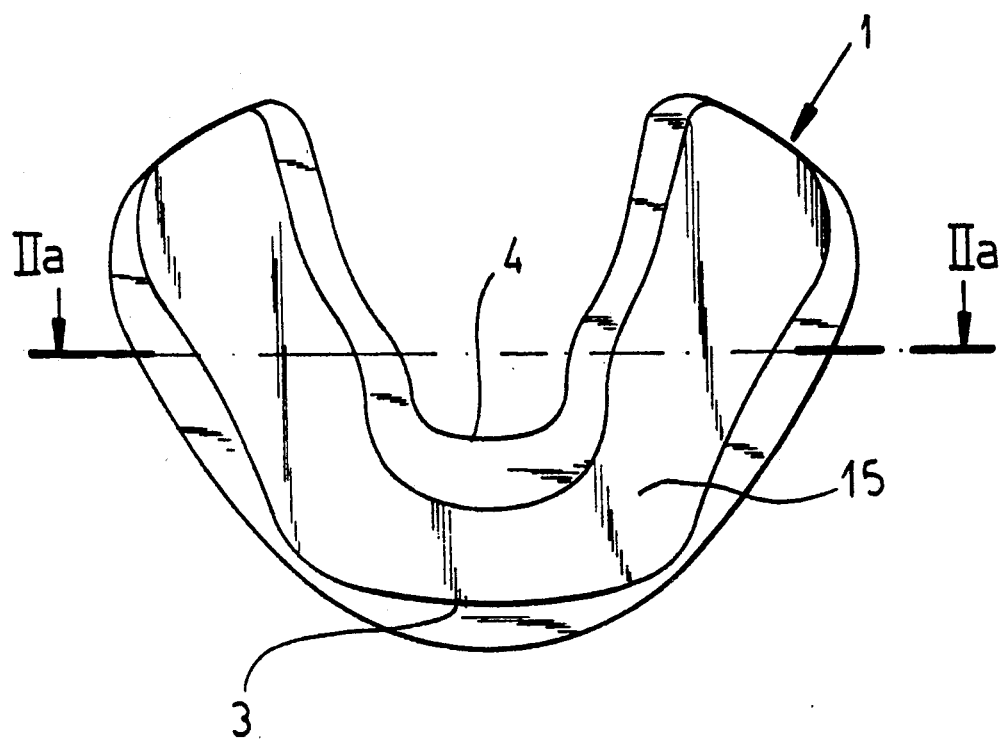
FIG. 1a is a top view of a lower-jaw impression tray.
Figure 2A:
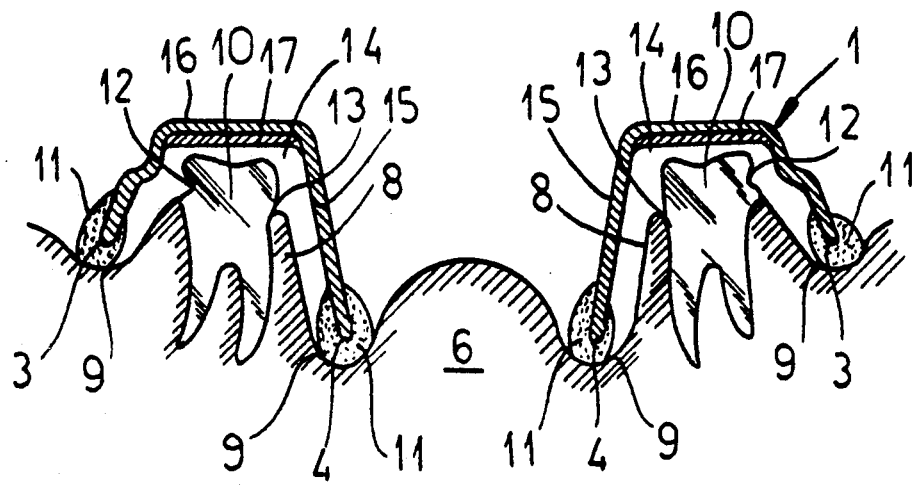
FIGS. 2a and 2b are sections taken respectively along lines IIa—IIa and IIb—IIb of respective FIGS. 1a and 1b but showing the impression tray when used according to the method of this invention.

As seen in FIGS. 1a and 2a a rigid metallic tray 1 for use on a lower jaw 6 basically has a wall 15 with an outer buccal edge 3 and an inner lingual edge 4 that meet at the rear ends of the tray 1 to form a downwardly open recess 14 surrounding teeth 10 formed with undercuts or recesses 12 and each having a marginal sulcus or gingival crevice 13. The patient's mouth also has a stationary mucosa 8 and a mobile mucosa 9 as described in by above-cited patent.

Figure 1B:
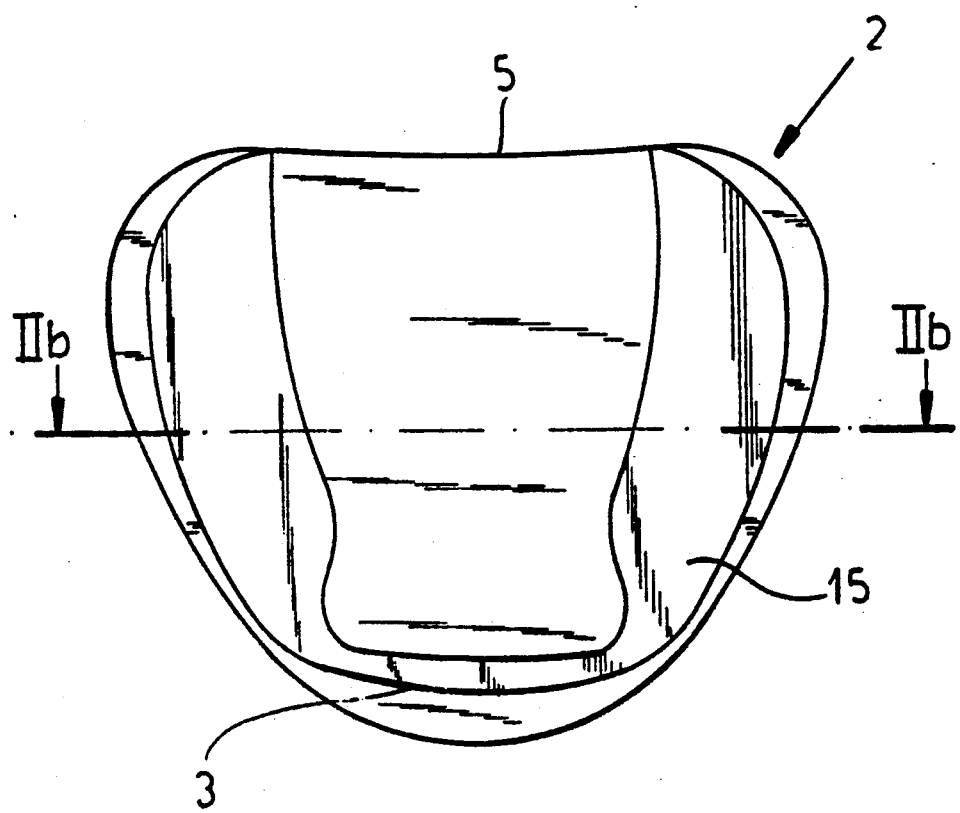
FIG. 1b is a bottom view of an upper-jaw impression tray.
Figure 2B:
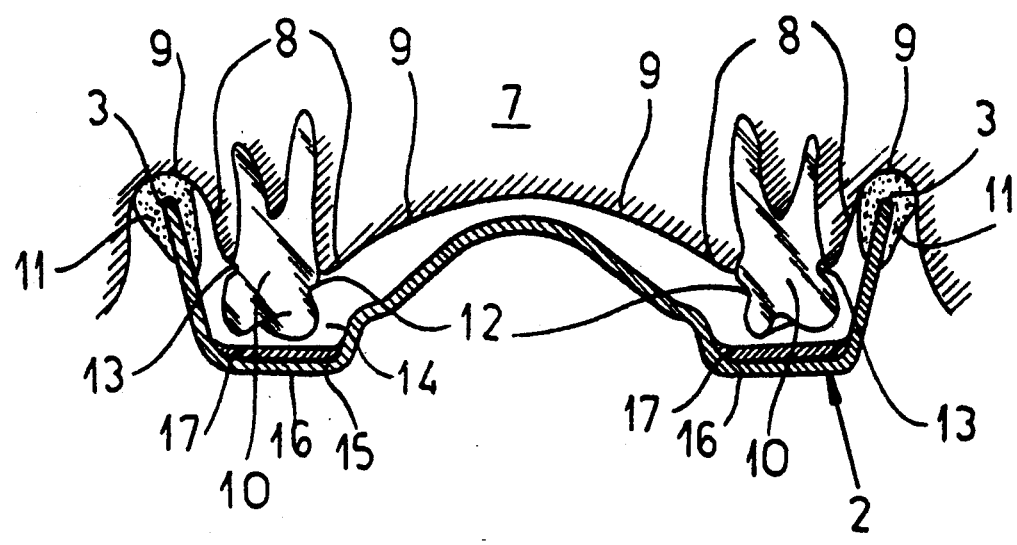

Similarly as seen in FIGS. 1b and 2b a rigid metallic tray 2 for use on an upper jaw 7 basically has an outer buccal edge 3 and a rear palatal edge 5 that meet at the rear ends of the tray 1 to form a downwardly open recess 14 surrounding teeth 10 formed with undercuts or recesses 12 and each having a marginal sulcus or gingival crevice 13.

According to this invention to form a fine-detail impression to start with a bead 11 of a high-viscosity impression material is applied all around the edges 3, 4, and 5 of the trays 1 and 2 and same are then pressed down over the respective dental arches. Thus the beads 11 engage the respective mobile mucosae 9 outsider the boundaries where they meet the respective stationary mucosae 8 and the patient works the mobile structures by thrusting out his tongue, pulling down his lips and cheeks so that the beads 11 conform to the underlying stationary structures.

The beads 11 are then allowed to cure. The result is that the trays 1 and 2 have been customized as regards their critical edges 3–5 to exactly fit the patient's mouth. The bases 16 of the trays 1 and 2 are then lined with a 2 mm to 3 mm thick layer 17 of a high-viscosity impression material and are filled atop these layers 17 with a low-viscosity impression material, and are put back in the patient's mouth. The material 17 has a disk consistency of 21.5 mm (US Specification ADA Spec. 19A). The mobile mucosae 9 are again activated and the trays 1 and 2 are pressed against the respective dental arches to force the high-viscosity lining layer 17 into the gingival crevices 13 while the lower-viscosity material otherwise fills the chambers 14 and flows into all the spaces and interstices of the gums and teeth.

The low- and high-viscosity materials merge and cure simultaneously and then the spoons 1 and 2 are pulled off the teeth 10. The low-viscosity material cures to a maximum Shore A hardness of 20. Since the bulk of the impression material is in fact formed by this low-viscosity material, such stripping will be fairly easy and at the same time the detail reproduction will be excellent.

All viscosities described above are taken with a Bohlin viscosimeter type 88 with measuring system no. 8 (spindle diameter 14 mm, beaker diameter 33 mm) with a drive rotation of between 0.67 to 0.75 sec$^{-1}$ at a measuring temperature of between 21.5° C. and 22.5° C.

I claim:

1. A method of taking an impression of a human patient's jaw having
    a hard U-shaped dental arch,
    a mobile mucosa and a stationary mucosa to each side of the arch,
    a linear action boundary between the mucosae, and
    at least one tooth projecting from the arch, with an imperforate tray forming a U-shaped recess and having an endless edge extending all around the recess, the method comprising the steps of sequentially:
    a) applying substantially only along the entire edge of the tray a bead of a high-viscosity impression material;
    b) fitting the tray with the bead of high-viscosity impression material to the jaw with the U-shaped recess engaging over the arch and the bead on the edge engaging and being deformed by the mobile mucosa outward of the linear action boundary
    c) curing the deformed bead of high-viscosity material and thereby forming the tray and the cured bead of high-viscosity material into a custom tray;

d) filling the custom tray with a body of a low-viscosity impression material;

e) pressing the filled custom tray over the patient's dental arch to press the cured bead on the tray edge into tight engagement against the mobile mucosa outward of the linear action boundary to form between the tray and the dental arch a substantially closed and generally constant-section chamber hydraulically confining the low-viscosity impression material;

f) compressing the confined low-viscosity material in the chamber against the dental arch by pressing the tray toward the arch while mobilizing the mobile mucosa to hydraulically press the confined material into form-fit engagement with the stationary mucosa and tooth and without substantial leakage of the impression material from the chamber;

g) curing the low-viscosity impression material; and h) stripping the custom tray with the low-viscosity material from the jaw.

2. The impression-taking method defined in claim 1 wherein the impression material is cured in step g) to a Shore A hardness of at most 30.

3. The impression-taking method defined in claim 2 wherein the impression material is cured in step g) to a Shore A hardness of at most 20.

4. The impression-taking method defined in claim 1 wherein the tray edge includes a buccal portion and a palatal/lingual portion, the bead being applied along both portions.

5. The impression-taking method defined in claim 1 wherein the high-viscosity impression material comprises polyvinylpolysiloxane having a viscosity when uncured of at least 200 Pa.sec and when cured of between 55 Shore A and 75 Shore A.

6. The impression-taking method defined in claim 1 wherein the low-viscosity impression material comprises polyvinylpolysiloxane having a viscosity when uncured of at most 160 Pa.sec and when cured of at most 30 Shore A.

7. The impression-taking method defined in claim 1, further comprising between steps c) and d) the step of d') lining at least a portion of the tray with a high-viscosity impression material, the low-viscosity material being filled in step d) over the lining of high-viscosity material.

8. The impression-taking method defined in claim 7 wherein during step g) both the high-viscosity lining material and the low-viscosity impression material are cured.

9. The impression-taking method defined in claim 7 wherein during step f) the high-viscosity lining material is forced into the sulcus of the tooth.

10. The impression-taking method defined in claim 7 wherein during step f) the high-viscosity lining material and the low-viscosity impression material are integrally merged.

11. The impression-taking method defined in claim 7 wherein the high-viscosity lining material is applied in a layer between 2 mm and 3 mm thick in the tray.

12. The impression-taking method defined in claim 7 wherein the high-viscosity impression material has a viscosity of more than 200 Pa.sec when uncured and about 50 Shore A when cured and the high-viscosity lining material has a viscosity of more than 200 Pa.sec and 30 Shore A when cured.

13. The impression-taking method defined in claim 7 wherein the high-viscosity lining material has a viscosity of more than 160 Pa.sec when uncured and about 30 Shore A when cured.

14. The impression-taking method defined in claim 1 wherein the tray is taken out of the patients mouth after step c) to fill it with the low-viscosity material in step d).

* * * * *